United States Patent
Boyle et al.

(10) Patent No.: US 6,582,448 B1
(45) Date of Patent: Jun. 24, 2003

(54) VESSEL OCCLUSION DEVICE FOR EMBOLIC PROTECTION SYSTEM

(75) Inventors: William J. Boyle, Fallbrook, CA (US); Andy E. Denison, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 232 days.

(21) Appl. No.: 09/746,790

(22) Filed: Dec. 21, 2000

(51) Int. Cl.$^7$ ............................................. A61M 29/00
(52) U.S. Cl. ....................................................... 606/200
(58) Field of Search ................................ 606/200, 191, 606/198, 194, 114, 127

(56) References Cited

U.S. PATENT DOCUMENTS

| | | | |
|---|---|---|---|
| 4,723,549 A | 2/1988 | Wholey et al. | |
| 4,997,435 A | 3/1991 | Demeter | |
| 5,100,425 A | 3/1992 | Fischell et al. | |
| 5,158,548 A | 10/1992 | Lau et al. | |
| 5,437,632 A | 8/1995 | Engelson | |
| 5,814,064 A | 9/1998 | Daniel et al. | |
| 5,827,324 A | 10/1998 | Cassell et al. | |
| 5,846,251 A | 12/1998 | Hart | |
| 5,911,734 A | 6/1999 | Tsugita et al. | |
| 5,980,555 A | 11/1999 | Barbut et al. | |
| 5,989,281 A | 11/1999 | Barbut et al. | |
| 6,168,579 B1 * | 1/2001 | Tsugita ................... | 606/200 X |
| 6,383,206 B1 * | 5/2002 | Gillick et al. ............... | 606/200 |
| 6,425,909 B1 * | 7/2002 | Dieck et al. ................ | 606/200 |
| 6,443,971 B1 * | 9/2002 | Boylan et al. .............. | 606/200 |

\* cited by examiner

*Primary Examiner*—Peter Nerbun
(74) *Attorney, Agent, or Firm*—Fulwider Patton Lee & Utecht, LLP

(57) ABSTRACT

A system used in a blood vessel when an interventional procedure is being performed in a stenosed or occluded region, which is capable of capturing embolic material which may be released into a blood vessel during a therapeutic interventional procedure at the site of a lesion in the blood vessel. The system is adapted to be utilized in a collateral blood supply system adapted to enable the flow of blood to bypass the blood vessel upon blocking thereof and to enable the reverse flow of blood through the blood vessel upon unblocking thereof. The system includes a guide wire, including a distal end, adapted to be positioned in a blood vessel relative to an interventional procedure site. A guide catheter, including a distal end, is adapted to enable the interventional procedure to be performed, and to be inserted over the guide wire and through a patient's vasculature to a position in the blood vessel relative to the interventional procedure site. An occluding device for occluding and blocking a blood vessel at a location relative to the interventional procedure site is adapted to be positionable at a location relative to he interventional procedure site, to be expandable so as to prevent and block the flow of blood past the occlusion, and to enable the capture of embolic material which may be released into the blood in the blood vessel during the therapeutic interventional procedure, and to be contracted to unblock the blood vessel and enable the recovery of captured embolic material.

19 Claims, 4 Drawing Sheets

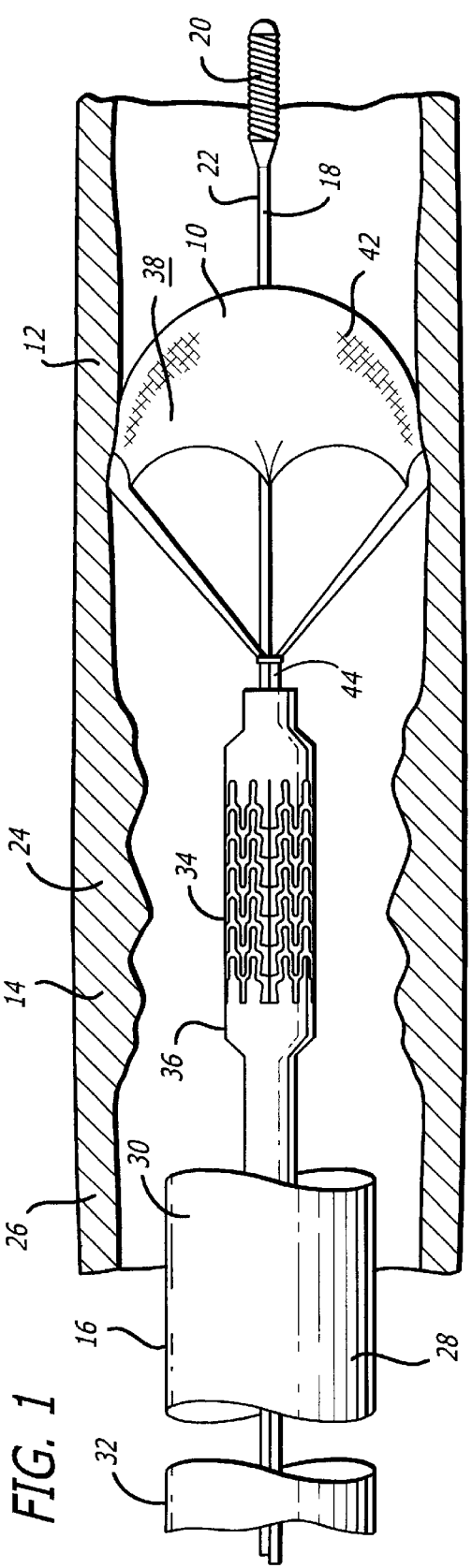
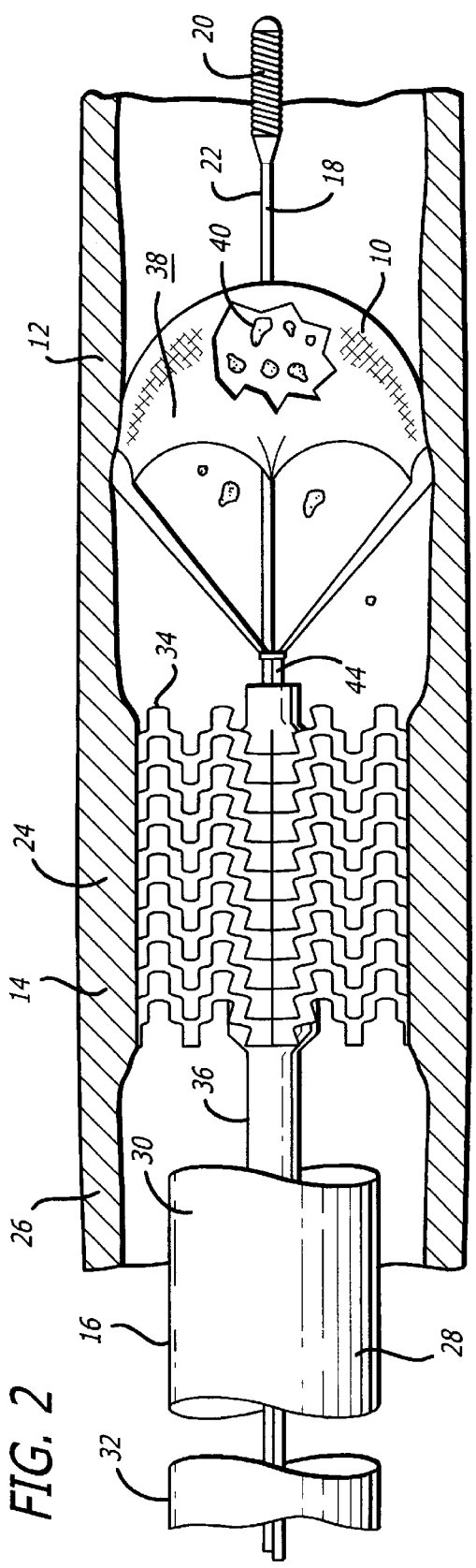

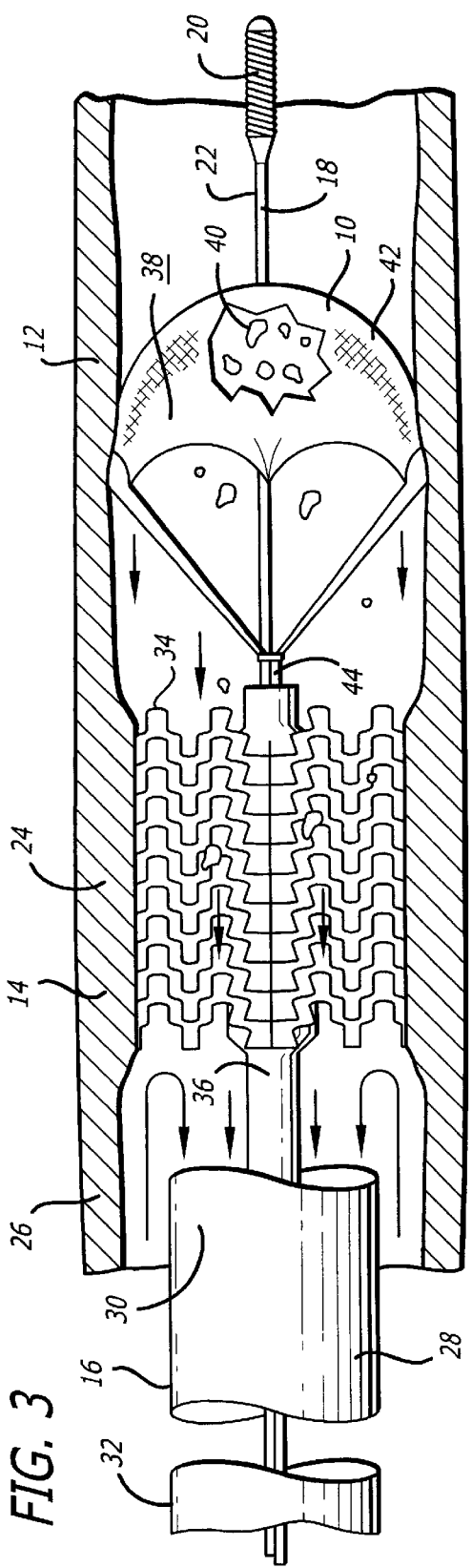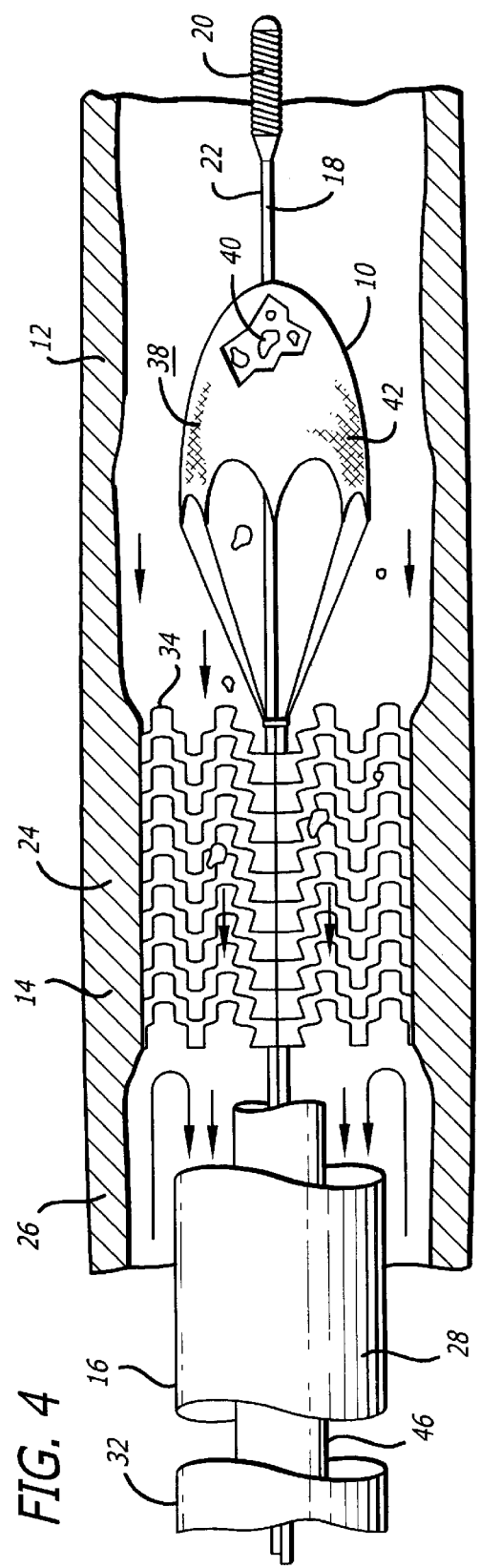

VESSEL OCCLUSION DEVICE FOR EMBOLIC PROTECTION SYSTEM

BACKGROUND OF THE INVENTION

The present invention relates generally to a system which can be used when an interventional procedure is being performed in a stenosed or occluded region of a blood vessel, including an occluding device adapted to capture embolic material that may be created and released into the bloodstream during the procedure. The system of the present invention is particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of a filter or trap downstream from the treatment site to capture embolic debris before it reaches the smaller blood vessels downstream. However, there have been problems associated with filtering systems, particularly since they have not always been able to remove all of the embolic material from the bloodstream. After crossing the stenosis and being positioned relative to the interventional procedure site, a device for enabling the removal of captured embolic material needs to be deployed, and after the interventional procedure has been performed, the device needs to be removed with the captured embolic material therein, in an efficient and effective manner.

What has been needed is a reliable system and method for treating stenosis in blood vessels which occludes the blood vessel at a location relative to the interventional procedure site, to enable the efficient capture of embolic material which may be released into the blood in the blood vessel during the therapeutic interventional procedure. The system and method should further be capable of enabling effective recovery of embolic material captured in the occluding device. The system and method should be relatively easy for a physician to use and should provide a nearly failsafe system capable of removing embolic debris released into the bloodstream. Moreover, such a system should be relatively easy to deploy and remove from the patient's vasculature. The inventions disclosed herein satisfy these and other needs.

SUMMARY OF INVENTION

The present invention provides a system and method for capturing and retaining embolic debris from a blood vessel which may be created during the performance of a therapeutic interventional procedure, such as a balloon angioplasty or stenting procedure, in order to prevent the embolic debris from lodging and blocking blood vessels downstream from the interventional site. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that any and all embolic debris is being collected and removed from the blood vessel when performing high-risk interventional procedures.

The present invention is deployed in the blood vessel at a location relative to the area of treatment in the interventional procedure site, occludes the blood to capture and retain any embolic debris which may be created during the interventional procedure, and recovers the emboli captured thereby.

In one aspect of the present invention, the system includes a guide catheter, and an occluding device adapted to occlude the blood vessel and to capture and retain embolic material. The emboli-capturing system of the present invention occludes blood flow through the area where the interventional procedure is to be performed and through the occluding device located relative to the interventional procedure site, which is designed to capture and retain friable plaque deposits. Additionally, the present invention enables the recovery of embolic material captured in the occluding device.

In an embodiment of the present invention, the system is adapted to capture embolic material which may be released into a blood vessel during a therapeutic interventional procedure at the site of a lesion in the blood vessel, in a collateral blood supply system adapted to enable the flow of blood to bypass the blood vessel upon blocking thereof and to enable the reverse flow of blood through the blood vessel upon unblocking thereof. The system includes a guide wire, including a distal end, adapted to be positioned in a blood vessel relative to an interventional procedure site. It further includes a guide catheter which includes a distal end, adapted to enable the interventional procedure to be performed, and adapted to be inserted over a guide wire and through a patient's vasculature to a position in the blood vessel relative to the interventional procedure site. It also includes an occluding device, adapted to occlude and block a blood vessel at a location relative to an interventional procedure site, to be expandable so as to prevent the flow of blood past the occlusion, and to enable the capture of embolic material which may be released into the blood in the blood vessel during a therapeutic interventional procedure. The occluding device is further adapted to be contracted to unblock the blood vessel and enable the recovery of captured embolic material. The system also includes a recovery system, for enabling the recovery of emboli captured in the occluding device. The recovery system includes a recovery device for enabling the recovery of the occluding device and embolic material captured in the occluding device. The occluding device includes a membrane comprised of a material without perfusion holes. The recovery device comprises a recovery sheath, adapted to extend through the elongated shaft of the guide catheter, and to be extendable about the occluding device to enable recovery of embolic material captured by the occluding device, by enabling the trapping therein of captured embolic material during the collapsing and removal of the occluding device.

In a further embodiment of the invention, the system is adapted to capture embolic material in a collateral blood supply system which comprises a vascular system which includes a plurality of vessels, including a common vessel which bifurcates into a pair of branch vessels. The guide catheter is adapted to be positionable in the common vessel relative to the interventional procedure site, and the interventional procedure site may be located in any one or more of the plurality of vessels, such as in one of the pair of branch vessels with the occluding device adapted to be positioned in the other of the pair of branch vessels.

Other features and advantages of the present invention will become more apparent from the following detailed description of the preferred embodiments of the invention, when taken in conjunction with the accompanying exemplary drawings.

BRIEF DESCRIPTION OF THE DRAWINGS

FIG. 1 is an elevational view, partially in section, depicting a first embodiment of the present invention disposed within the internal carotid artery of a patient, wherein an occluding device is in expanded condition, and an expandable interventional instrument is unexpanded.

FIG. 2 is an elevational view, partially in section, of the first embodiment shown in FIG. 1, wherein the occluding device and the expandable interventional instrument are in expanded condition and embolic material released during the therapeutic interventional procedure is shown.

FIG. 3 is an elevational view, partially in section, of the first embodiment shown in FIGS. 1 and 2, including arrows indicating the direction of recovery of the embolic material, wherein the occluding device is in expanded condition.

FIG. 4 is an elevational view, partially in section, of the first embodiment shown in FIGS. 1–3, including arrows indicating the direction of recovery of the embolic material, wherein the occluding device is in collapsing condition.

DETAILED DESCRIPTION OF THE PREFERRED EMBODIMENTS

Figure 5:
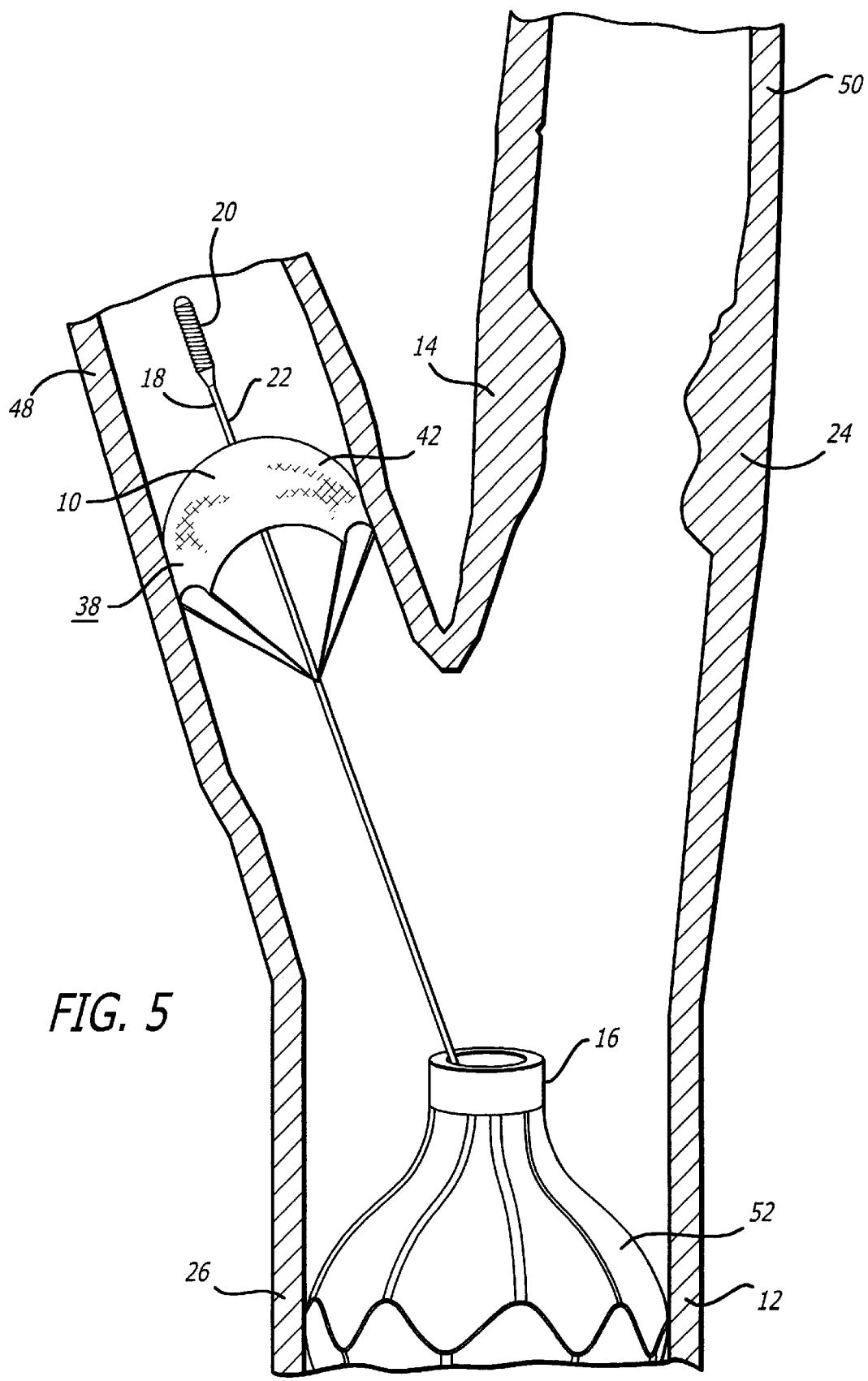
FIG. 5 is an elevational view, partially in section, depicting a second embodiment of the invention disposed within a carotid artery bifurcated vascular system of a patient, wherein a guide catheter is positioned in a common vessel, an occluding device is positioned in a first branch vessel, and a lesion is located in a second branch vessel.

One aspect of the invention is an improved system and method for efficiently and effectively enabling a therapeutic procedure to be performed in a blood vessel at an interventional procedure site (e.g., stenosis site due to plaque), adapted to occlude the blood vessel at a location relative to the interventional procedure site, to prevent the flow of blood past the occlusion, and to enable the capture of embolic material which may be released into the blood vessel during the interventional procedure, and to enable recovery of the captured emboli. The embodiments of the improved system and method are illustrated and described herein by way of example only and not by way of limitation. While the present invention is described in detail as applied to the carotid arteries of the patient, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as stenting, balloon angioplasty, laser angioplasty or atherectomy.

Referring now to the drawings, wherein like reference numerals denote like or corresponding parts throughout the drawing figures, and particularly to the embodiment of the invention as shown in FIGS. 1–6, an exemplary system 10 is provided for enabling an interventional procedure to be performed in a blood vessel 12 at an area of treatment 14. The system 10 is adapted to be operable, for example, in a collateral blood supply system which includes the blood vessel 12. The collateral blood supply system is adapted to enable the flow of blood to bypass the blood vessel 12 upon blocking thereof, and to enable the reverse flow of blood through the blood vessel 12. The collateral blood supply system may comprise a vascular system which includes a plurality of vessels, including a common vessel which bifurcates into a pair of branch vessels. The vascular system may for example comprise the carotid artery, wherein the common vessel comprises the common carotid vessel, a first branch vessel comprises the external carotid artery, and a second branch vessel comprises the internal carotid artery. The blood vessel 12 may comprise for example the common carotid vessel.

The system 10 includes a guide catheter 16, adapted to guide the delivery of the elements for enabling the interventional procedure to be performed, and to guide the removal of the elements to be retrieved after performing the interventional procedure. As shown in FIGS. 1 and 2, the guide catheter 16 may be placed within the blood vessel 12 of the patient and guided into position by riding over or being fixed to a guide wire 18. The guide wire 18 may include a coiled tip 20 at a distal end 22 thereof. The blood vessel 12 may include the area of treatment 14 therein, which may comprise the interventional procedure site, wherein atherosclerotic plaque 24 may have built up against the inside wall 26, which decreases the diameter of the blood vessel 12. As a result, blood flow may be diminished through this area. The guide catheter 16 may include an elongated shaft 28 having a distal end 30 and a proximal end 32.

The therapeutic interventional procedure may comprise positioning, expanding, and implanting an expandable interventional instrument 34, such as a stent, at the interventional procedure site 14, to press the build-up of plaque 24 of the stenosis against the inside wall 26 of the blood vessel 12, to increase the diameter of the occluded area 14 of the blood vessel 12, and to help restore sufficient flow of blood to the downstream vessels leading to the brain. The stent 34 may be delivered to the interventional procedure site by a delivery system 36 extendable through the guide catheter 16. The stent 34 may not only help increase the diameter of the occluded area, but may help prevent restenosis in the area of treatment 14. The delivery system 36 may further be adapted to enable the stent 34 to be expanded and deployed at the interventional procedure site 14.

A device 38 for occluding and blocking a blood vessel 12 may be positioned at a location relative to the interventional procedure site 14. The occluding device 38 may be further adapted to prevent and block the flow of blood past the occlusion, to enable the capture of embolic material 40 which may be released into the blood in the blood vessel 12 during the therapeutic interventional procedure, and to be contracted to unblock the blood vessel 12 and enable the recovery of captured embolic material 40. The occluding device 38 may comprise an expandable balloon or basket, and may include a membrane 42 extending thereabout which may be comprised of a material without perfusion holes, such as for example a solid non-porous membrane, to prevent and block blood flow through the blood vessel 12. A wire 44, to which the occluding device 38 may be connected, may be adapted to extend through the guide catheter 16 to position the occluding device 38 in the blood vessel 12. While the occluding device 38 would prevent blood and emboli from flowing up through the blood vessel 12, a valve at the end of the guide catheter 16 is adapted to be opened to enable flushing of embolic material through the guide catheter 16. The locations of the occluding device 38 and the distal end 22 of the guide wire 18 relative to the interventional procedure site 14 may comprise positions distal to the interventional procedure site 14.

As seen in FIGS. 3 and 4, the system 10 further includes a recovery device 46, which may comprise a recovery sheath, adapted to recover embolic material 40 captured in the occluding device 38. The recovery device 46 may be adapted, upon deployment of the stent 34 and retrieval of the delivery system 36, to be extendable through the guide catheter 16, and to extend about and collapse the occluding device 38 so as to trap therein emboli 40 captured in the occluding device 38. The elongated shaft 28 of the guide catheter 16 may be adapted to enable recovery of embolic material 40 upon opening a valve at the proximal end 32 of the guide catheter 16. The valve at the proximal end 32 of the guide catheter 16 is adapted to be opened during crossing of the lesion 24 by the interventional instrument 34 to enable the flushing of embolic material 40 through the guide catheter 16. The system 10 may further include a retrieving device, for enabling the retrieving of embolic material 40 at the conclusion of the therapeutic interventional procedure. The retrieving device may comprise a vacuum syringe, and may be adapted to be connected to the proximal end 32 of the elongated shaft 28 of the guide catheter 16, to apply a vacuum and suction out embolic material 40.

Figure 6:
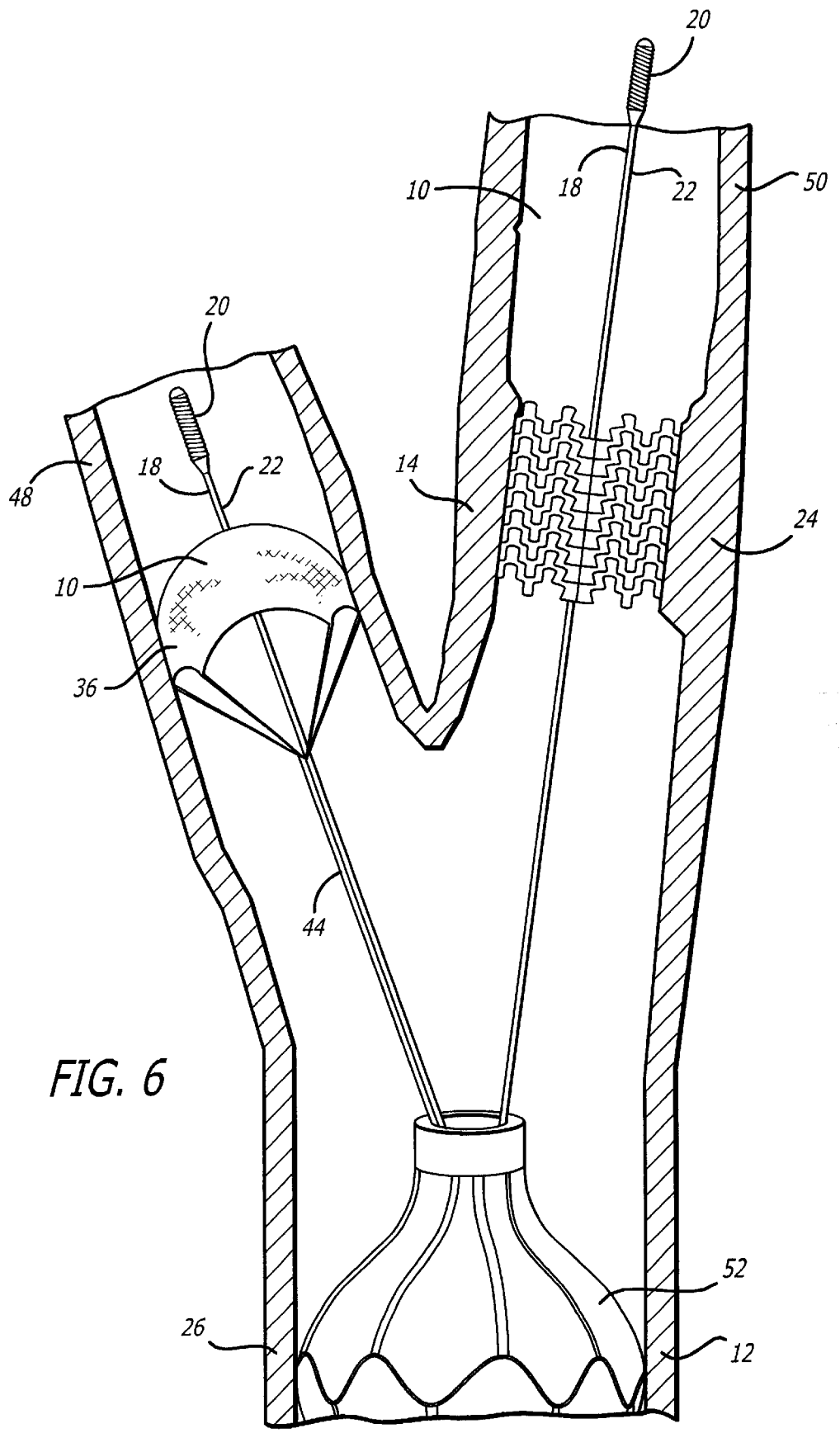
FIG. 6 is an elevational view, partially in section, depicting a second embodiment of the invention disposed within a carotid artery bifurcated vascular system of a patient, wherein a guide catheter is positioned in a common vessel, an occluding device is positioned in a first branch vessel, a lesion is located in a second branch vessel, and an expandable interventional instrument is in expanded condition in the second branch vessel.

As illustrated in FIGS. 5–6, the collateral blood supply system comprises a vascular system including a plurality of vessels, which include a common vessel comprising the blood vessel 12, and a pair of branch vessels including a first branch vessel 48, and a second branch vessel 50. A single interventional procedure site 14 or multiple sites may be located in one or more of the plurality of vessels, and is shown for example in FIGS. 5 and 6 in the second branch vessel 50. The guide catheter 16 may include an occluding device 52 at the distal end thereof, for occluding and blocking the blood vessel 12, which occluding device 52 may comprise a basket for example.

In use, as illustrated in FIGS. 1–6, the system 10 may be positioned in the patient's vasculature utilizing any one of a number of different methods. In one preferred method, the guide catheter 16 may be placed in the blood vessel 12 by utilizing the guide wire 18 which is inserted into the patient's vasculature and manipulated by the physician to a location relative to the area of treatment 14. Thereafter, once the guide wire 18 is in place, the guide catheter 16 may be maneuvered over the guide wire 18 (via a central lumen) using well-known over-the-wire techniques to place the guide catheter 16 at a location relative to the area of treatment 14. The delivery system 36 for delivery of the stent 34 to the interventional procedure site 14 may be guided through the guide catheter 16, and the occluding device 38, connected to the distal end of wire 44, may also be guided through the guide catheter 16 to a position at a location relative to the area of treatment 14. The occluding device 38 may then be expanded within the blood vessel 12, so as to prevent and block the flow of blood past the occluding device 38, and to enable the capture in the occluding device 38 of embolic material 40 which may be released during the therapeutic interventional procedure. The stent 34 may then be expanded at the interventional procedure site 14, after which the delivery system 36 may be retracted through the guide catheter 16.

During crossing of the lesion 24 by the interventional instrument 34, embolic material 40 may be released, and the valve at the proximal end 32 of the guide catheter 16 may be opened to enable the flushing of embolic material 40. After the interventional procedure is performed, the occluding device 38 may enable the capture of embolic material 40 therein which may be released into the blood vessel 12 during the interventional procedure. A vacuum syringe may be connected to the proximal end of the guide catheter 32, to apply a vacuum and suction out embolic material 40. The recovery sheath 46 may then be guided through the guide catheter 16 so as to extend about and collapse the occluding device 38, to retain embolic material 40 captured in the occluding device 38. The recovery sheath 46 with the occluding device 38 contained therein may be retrieved, and the guide catheter 16 may be withdrawn from the blood vessel 12.

As shown in FIGS. 1–4, wherein the interventional procedure site 14 is located in the blood vessel 12, the occluding device 38 is positioned in the blood vessel 12 at a location distal to the interventional procedure site 14, and expanded to prevent and block blood flow therethrough. With blood flow through the blood vessel 12 prevented and blocked by the occluding device 38, emboli will not pass distal of the expanded occluding device 38. The therapeutic interventional procedure may then be performed at the interventional procedure site 14, as by expanding the stent 36. Upon completion of the therapeutic interventional procedure, emboli are aspirated through the guide catheter 16. The occluding device 38 may be contracted to unblock the blood vessel 12 and enable the recovery of captured embolic material 40.

As seen in FIGS. 5–6, wherein the interventional procedure site 14 is located in the second branch vessel 50, for example, the occluding device 38 is positioned in the first branch vessel 48 at a location relative to the interventional procedure site 14, and expanded to prevent and block blood from flowing through the first branch vessel 48. The occluding device 52, positioned in the common vessel 12 at a location relative to the interventional procedure site 14, may be expanded to prevent and block blood from flowing therethrough in the common vessel 12, which blood flow through the guide catheter 16 in the common blood vessel 12 may be enabled by opening the valve at the proximal end 32 of the elongated shaft 28. The occluding device 52 could also be configured to extend distal of the guide catheter 16, so as to form a funnel shaped entry into the guide catheter 16, to allow for unobstructed emboli flow into the guide catheter 16. With blood flow through the first branch vessel 48 prevented and blocked by the occluding device 38, and blocked through the occluding device 52 while enabled through the guide catheter 16 in the common vessel 12, the collateral blood supply system would enable the blood flow to bypass the first branch vessel 48. The therapeutic interventional procedure may then be performed at the interventional procedure site 14, as by expanding the stent 36. The valve on the guide catheter 16 would be opened and a syringe attached allowing any embolic material to be aspirated into the guide catheter 16. Upon completion of the therapeutic interventional procedure, the occluding device 38 may then be contracted and retrieved to unblock the first branch vessel 48.

It should be appreciated that the particular embodiments of the occluding device 38 and the recovery device 46 are capable of being positioned in the blood vessels. However, other forms of the occluding device 38 and the recovery device 46 may be utilized with the present invention without departing from the spirit and scope of the invention. For example, the occluding device 38 and the recovery device 46 may further be comprised of other materials. Additionally, while the occluding device 38 and the recovery device 46 are shown in various shapes in the embodiments herein, it can be formed in any one of a number of different shapes depending upon the construction desired. Based on the present disclosure, other adhesives and applications are known to one skilled in the art.

Further, the various components may be joined by suitable adhesives such as acrylonitrile based adhesives or cyanoacrylate based adhesives. Heat shrinking, heat bonding, or ultrasonic welding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the effectiveness of performing interventional procedures by preventing the flow of blood past the occlusion, and enabling the capture and recovery of embolic material. Further modifications and improvements may additionally be made to the system and method disclosed herein without the departing from the scope of the invention. Accordingly, it is not intended that the invention be limited by the specific description of the embodiments.

What is claimed:

1. A system for capturing embolic material which may be released into a blood vessel during a therapeutic interventional procedure by an interventional instrument at the site of a lesion in the blood vessel, in a collateral blood supply system adapted to enable the flow of blood to bypass the blood vessel upon blocking thereof and to enable the reverse flow of blood through the blood vessel upon unblocking thereof, comprising:

a guide wire, including a distal end, adapted to be positioned in a blood vessel in a collateral blood supply system relative to an interventional procedure site;

a guide catheter, including a distal end, adapted to enable the interventional procedure to be performed, and adapted to be inserted over the guide wire and through a patient's vasculature to a position in the blood vessel relative to the interventional procedure site; and an occluding device for occluding and blocking the blood vessel in the collateral blood supply system, adapted to be positionable at a location relative to the interventional procedure site, to be expandable so as to prevent and block the flow of blood past the occlusion and to enable the capture of embolic material which may be released into the blood in the blood vessel during the therapeutic interventional procedure by an interventional instrument, and to be contracted to unblock the blood vessel and enable the recovery of any residual embolic material, comprised of a material without perfusion holes.

2. The system of claim 1, wherein the position of the occluding device relative to the interventional procedure site comprises a position distal to the interventional procedure site.

3. The system of claim 1, further comprising a recovery system for enabling the recovery of embolic material.

4. The system of claim 1, wherein the collateral blood supply system comprises a vascular system which includes a plurality of vessels, including a common vessel which bifurcates into a pair of branch vessels, the guide catheter is adapted to be positionable in the common vessel relative to the interventional procedure site, and the interventional procedure site is located in at least one of the plurality of vessels.

5. The system of claim 1, wherein the distal end of the guide catheter includes an occluding device for occluding and blocking a blood vessel.

6. The system of claim 1, further comprising an interventional instrument, and a system for delivering the interventional instrument to the interventional procedure site, and for enabling the interventional instrument to be deployed at the interventional procedure site.

7. The system of claim 1, wherein the occluding device comprises an expandable balloon, which comprises the membrane.

8. The system of claim 1, wherein the occluding device comprises a basket which includes the membrane extending thereabout.

9. The system of claim 1, wherein the material without perfusion holes comprises a solid non-porous membrane.

10. The system of claim 3, wherein the recovery system includes a recovery device, for enabling the recovery of the occluding device and embolic material captured in the occluding device.

11. The system of claim 4, wherein the interventional procedure site is located in one of the pair of branch vessels, and the occluding device is adapted to be positioned in the other of the pair of branch vessels.

12. The system of claim 4, wherein the blood supply flow reversal system is adapted to enable anatomical contralateral blood supply flow.

13. The system of claim 10, wherein the guide catheter further includes an elongated shaft, and the recovery device comprises a recovery sheath, adapted to extend through the elongated shaft of the guide catheter, and to be extendable about and collapse the occluding device to enable the trapping therein and recovery of embolic material captured by the occluding device, by enabling the removal of the occluding device.

14. The system of claim 10, wherein the guide catheter further includes a proximal end, and the recovery system further includes a vacuum syringe, adapted to be connected to the proximal end of the guide catheter, to apply a vacuum and suction out embolic material therethrough at the conclusion of the therapeutic interventional procedure.

15. The system of claim 11, further comprising an occluding device located at the distal end of the guide catheter, and adapted to be positionable in the common vessel.

16. The system of claim 11, wherein the occluding device is adapted to form a generally funnel shaped configuration so as to enable embolic material to substantially freely pass into the guide catheter.

17. The system of claim 12, wherein the vascular system comprises the carotid artery.

18. A system for capturing embolic material which may be released into a blood vessel during a therapeutic interventional procedure at the site of a lesion in the blood vessel, in a collateral blood supply system adapted to enable the flow of blood to bypass the blood vessel upon blocking thereof and to enable the reverse flow of blood through the blood vessel upon unblocking thereof, comprising:

a guide wire, including a distal end, adapted to be positioned in a blood vessel in a collateral blood supply system relative to an interventional procedure site;

a guide catheter, including a distal end, adapted to enable the interventional procedure to be performed, and adapted to be inserted over the guide wire and through a patient's vasculature to a position in the blood vessel relative to the interventional procedure site; and means for occluding and blocking the blood vessel in the collateral blood supply system, adapted to be positionable at a location relative to the interventional procedure site, to be expandable so as to prevent and block the flow of blood past the occlusion and to enable the capture of embolic material which may be released into the blood in the blood vessel during the therapeutic interventional procedure, and to be contracted to unblock the blood vessel and enable the recovery of captured embolic material, comprised of a material without perfusion holes.

19. A method of capturing embolic material which may be released into a blood vessel during a therapeutic interventional procedure at the site of a lesion in the blood vessel, in a collateral blood supply system adapted to enable the flow of blood to bypass the blood vessel upon blocking thereof and to enable the reverse flow of blood through the blood vessel upon unblocking thereof, in a system which comprises a guide wire, including a distal end, adapted to be positioned in a blood vessel in a collateral blood supply system relative to an interventional procedure site, a guide catheter, including a distal end, adapted to enable the interventional procedure to be performed, and adapted to be inserted over the guide wire and through a patient's vasculature to a position in the blood vessel relative to the interventional procedure site, and an occluding device for occluding and blocking the blood vessel in the collateral blood supply system, adapted to be positionable at a location relative to the interventional procedure site, to be expandable so as to prevent and block the flow of blood past the occlusion and to enable the capture of embolic material which may be released into the blood in the blood vessel during the therapeutic interventional procedure, and to be contracted to unblock the blood vessel and enable the recovery of any residual embolic material, comprised of a material without perfusion holes, wherein the method comprises:

inserting the guide wire into the blood vessel such that the occluding device is positioned at a location relative to the interventional procedure site; and expanding the occluding device, comprised of a material without perfusion holes, within the blood vessel in the collateral blood supply system at the location relative to the interventional procedure site, so as to prevent and block the flow of blood past the occluding device, and to enable the capture in the occluding device of embolic material which may be released into the blood vessel during the therapeutic interventional procedure.

* * * * *

UNITED STATES PATENT AND TRADEMARK OFFICE
CERTIFICATE OF CORRECTION

PATENT NO.    : 6,582,448 B1
DATED         : June 24, 2003
INVENTOR(S)   : William J. Boyle et al.

It is certified that error appears in the above-identified patent and that said Letters Patent is hereby corrected as shown below:

<u>Title page,</u>
Item [75], Inventors, add the following co-inventor:
-- Paul F. Muller, San Carlos; --.

Signed and Sealed this

Eighteenth Day of January, 2005

JON W. DUDAS
*Director of the United States Patent and Trademark Office*